(12) United States Patent
Weiss et al.

(10) Patent No.: US 10,194,838 B2
(45) Date of Patent: Feb. 5, 2019

(54) LANCING DEVICE

(71) Applicant: ROCHE DIABETES CARE, INC., Indianapolis, IN (US)

(72) Inventors: Thomas Weiss, Mannheim (DE); Susanne Gentsch, Viernheim (DE); Lydia Kolonko, Heppenheim (DE); Richard Forster, Fensterbach (DE); Andreas Gorshöfer, Steinberg am See (DE); Karl-Peter Ebert, Fränkisch-Crumbach (DE); Robert Wessel, Schwarmstedt (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 147 days.

(21) Appl. No.: 15/279,674

(22) Filed: Sep. 29, 2016

(65) Prior Publication Data

US 2017/0014054 A1 Jan. 19, 2017

Related U.S. Application Data

(63) Continuation of application No. 12/576,795, filed on Oct. 9, 2009, now Pat. No. 9,480,419.

(30) Foreign Application Priority Data

Oct. 9, 2008 (EP) ...................................... 08017714

(51) Int. Cl.
*A61B 5/15* (2006.01)
*A61B 5/151* (2006.01)
*A61B 5/157* (2006.01)

(52) U.S. Cl.
CPC ............ *A61B 5/1411* (2013.01); *A61B 5/157* (2013.01); *A61B 5/1513* (2013.01);
(Continued)

(58) Field of Classification Search
CPC ............ A61B 5/1411; A61B 5/150183; A61B 5/1513; A61B 5/15117; A61B 5/150412;
(Continued)

(56) References Cited

U.S. PATENT DOCUMENTS

RE35,803 E 5/1998 Lange et al.
5,916,230 A 6/1999 Brenneman et al.
(Continued)

FOREIGN PATENT DOCUMENTS

EP 1 032 307 B1 5/2007
EP 0 885 590 B1 1/2008
(Continued)

*Primary Examiner* — Anh T Dang
(74) *Attorney, Agent, or Firm* — Bose McKinney & Evans LLP

(57) ABSTRACT

A lancing device comprises a lancet drive to cause a lancet to effect a puncturing movement, a housing that encloses the lancet drive, and a touching element with an opening for applying a part of a body in which a prick wound is to be produced, the touching element being movable relative to the lancet drive for the purpose of adjusting the puncturing depth in a puncturing direction. The touching element is connected rotatably by means of a screw thread to an intermediate piece and is movable in the puncturing direction, while the intermediate piece is rotatable and movable relative to the housing. A guide prevents rotation of the touching element relative to the housing, and the touching element is enclosed by the intermediate piece at least over part of its length.

29 Claims, 3 Drawing Sheets

(52) U.S. Cl.
CPC .... *A61B 5/150022* (2013.01); *A61B 5/15113* (2013.01); *A61B 5/15117* (2013.01); *A61B 5/15163* (2013.01); *A61B 5/150183* (2013.01); *A61B 5/150305* (2013.01); *A61B 5/150412* (2013.01); *A61B 5/150503* (2013.01); *A61B 5/150358* (2013.01)

(58) Field of Classification Search
CPC ................ A61B 5/157; A61B 5/15163; A61B 5/150022; A61B 5/15113; A61B 5/150503
See application file for complete search history.

(56) References Cited

U.S. PATENT DOCUMENTS

| | | | |
|---|---|---|---|
| 6,022,366 | A | 2/2000 | Schraga |
| 6,379,317 | B1 | 4/2002 | Kintzig et al. |
| 6,645,219 | B2 | 11/2003 | Roe |
| 7,651,612 | B2 | 1/2010 | Berthold |
| 2003/0187470 | A1 | 10/2003 | Chelak et al. |
| 2005/0125019 | A1 | 7/2005 | Kudrna et al. |
| 2006/0155215 | A1 | 7/2006 | Cha et al. |
| 2006/0155317 | A1 | 7/2006 | List |
| 2007/0055298 | A1 | 3/2007 | Uehata et al. |
| 2007/0233167 | A1 | 10/2007 | Weiss et al. |

FOREIGN PATENT DOCUMENTS

| | | |
|---|---|---|
| EP | 1 669 028 B1 | 1/2008 |
| EP | 1 427 327 B1 | 2/2008 |
| WO | WO 03/022130 A2 | 3/2003 |
| WO | WO 2006/027101 A1 | 3/2006 |

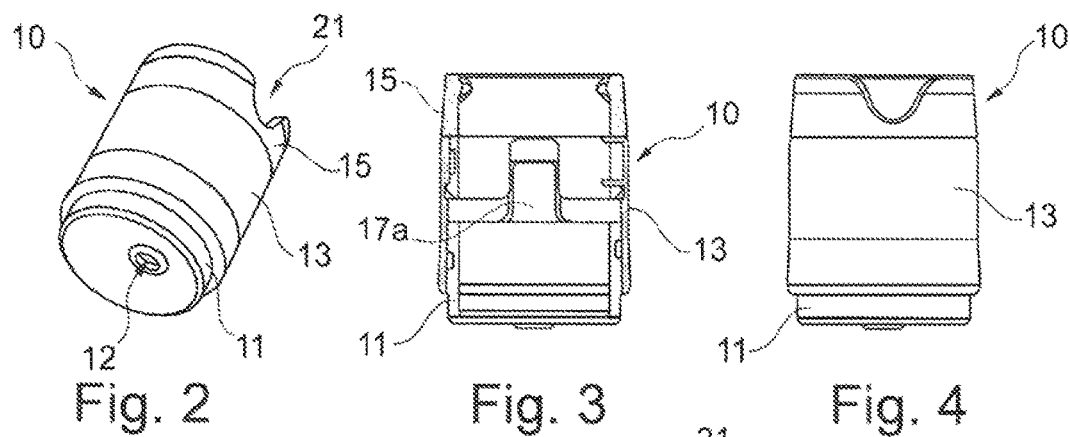
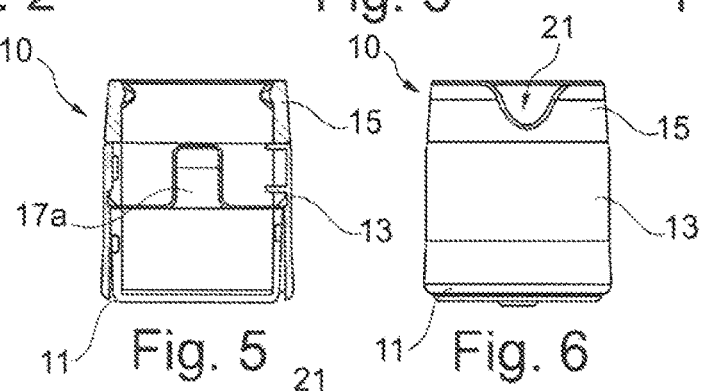
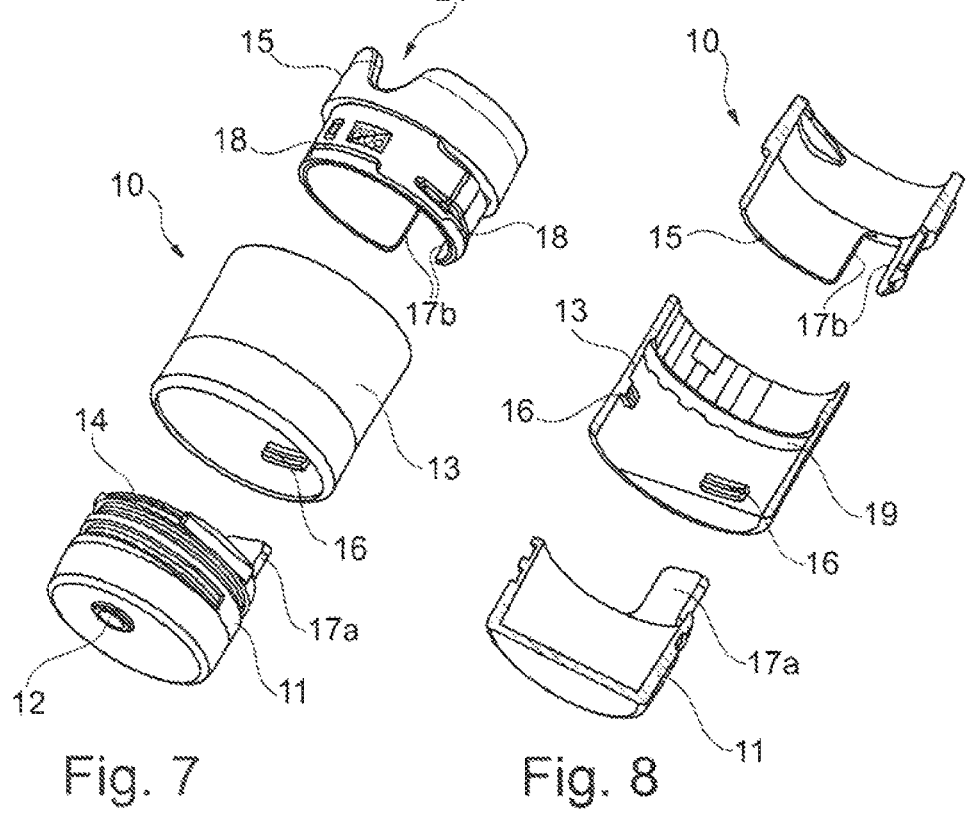

LANCING DEVICE

RELATED APPLICATIONS

This application is a continuation of U.S. patent application Ser. No. 12/576,795 filed Oct. 9, 2009, which claims priority to EP 08017714.0 filed Oct. 9, 2008, both of which are hereby incorporated herein by reference in their entireties.

BACKGROUND

Field of the Invention

The present invention relates to the field of lancing devices.

Description of Related Art

For taking a small quantity of body fluid, for example blood and/or interstitial fluid, from a part of a body, for example a finger, for analytic-diagnostic purposes, one normally uses lancets by which the corresponding part of the body is punctured using a lancing system to produce a prick wound.

In order to make such sampling as efficient and least painful as possible, lancing devices usually allow the puncturing depth to be adjusted and, accordingly, to be adapted to a user's personal requirements. On the one hand the puncturing depth must be sufficiently great to allow a sufficient quantity of body liquid to be withdrawn, while on the other hand it should be as small as possible in order to prevent unnecessary pain.

EP 1 427 327 B1 discloses a lancing device where the position of a stop can be adjusted inside the device to stop the puncturing movement and, accordingly, to limit the travel to the length necessary to reach the desired puncturing depth. It is a disadvantage of that arrangement that when the movement of the lancet is interrupted by the stop this may give rise to vibrations that may lead to painful transverse movements of the lancet.

U.S. Pat. No. 6,022,366 describes a lancing device where the length of a lancet holder can be adapted to adjust the puncturing depth. This requires, however, that a cap of the housing has to be removed first, which may be connected with difficulties for many users. Further, this presents the risk of the user being hurt by a lancet present in the device.

U.S. Publication No. 2007/0055298 A1 discloses a lancing device where a screwed-on end cap is used for adjusting the puncturing depth. That end cap serves as a touching element and has an opening that can be placed on that part of the body in which a prick wound is to be produced. When the screwed-on cap is turned, it moves relative to the lancet drive of the unit, in the puncturing direction, so that a desired puncturing depth can be adjusted. However, it is a disadvantage of that arrangement that a gap forms between the cap and the device housing when the cap is moved away from the housing in the puncturing direction by a screwing movement. Such a gap is difficult to clean. In addition, contaminations tend to accumulate in such a gap.

Accordingly, there has been a need in the art for a puncturing depth adjusting feature that can be realized in a lancing device without giving rise to the disadvantages described above.

SUMMARY

It is against the above background that the present invention provides certain unobvious advantages and advancements over the prior art. In particular, the inventors have recognized a need for improvements in lancing devices. Although the present invention is not limited to specific advantages or functionality, it is noted that one embodiment of the present invention is based on a lancing device having the features set forth in claim 1. Advantageous further developments of the invention are the subject matter of the remainder of the claims. An embodiment of the claimed invention also relates to a puncturing depth adjusting unit for a lancing device.

In a lancing device according to the invention, the puncturing depth is adjusted by varying the position of a touching element relative to a lancet drive. It is an advantage of that arrangement that the travel can remain the same for every puncturing action of the lancet, irrespective of the desired puncturing depth. Premature stopping of a lancet, which might cause painful vibrations, can be avoided in this way.

The touching element of a lancing device according to the invention is connected to an intermediate piece via a thread so that it can rotate and thereby move in the puncturing direction. The intermediate piece is rotatable and movable relative to the housing. Adjusting a desired puncturing depth by rotation of the intermediate piece relative to the touching element therefore can be effected even by a user whose manual mobility is limited due to age or illness. That turning movement causes the touching element to be moved in the puncturing direction, relative to the lancet drive. As a result of that movement, the spacing between the touching element and the lancet drive and, accordingly, the adjusted puncturing depth, changes. Preferably, the turning movement simultaneously has the effect to change the spacing between the touching element and the housing. In principle, however, it is also possible to mount the lancing drive movably in the housing so that the spacing between the touching element and the housing will not necessarily be changed by the turning movement.

Using the intermediate piece according to the invention has the advantageous effect to prevent a gap, in which contaminations might accumulate and which would be difficult to clean, from forming between the touching element and the housing.

A turning movement of the touching element relative to the housing is prevented by a guide. By preventing a turning movement of the touching element relative to the housing it is ensured that the touching element and, especially, its opening will always retain the same orientation relative to the lancet drive of the lancing device. This is important for lancing devices that use a rotary magazine comprising a plurality of lancets, as the opening of the touching element must be aligned for each puncturing operation flush with the respective lancet of the rotary magazine coupled to the lancet drive.

The guide may, for example, have a guide element that extends in the puncturing direction and is arranged between two stops relative to which it is movable in the puncturing direction. The guide element may, for example, be configured as a lug or feather disposed on the touching element. There is also the possibility to dispose the stops on the touching element and to provide that a guide element, arranged rigidly on the housing, projects into the space between those stops.

A lancing device containing a receptacle for a rotary magazine has been known, for example, from EP 1 669 028 A1, which in this respect is incorporated by reference into the present application, especially with respect to possible embodiments of a rotary magazine and of a lancing drive cooperating with the latter. Preferably, the receptacle is arranged in a puncturing depth adjusting unit constituted by the touching element and the intermediate piece.

The screw thread by means of which the touching element is rotatably mounted on the intermediate piece may be arranged on the touching element and/or on the intermediate piece. It is sufficient for this purpose to provide a groove or notch in the form of a thread in one of the two elements. As to the counter thread, a single projection, engaging that thread, will already be sufficient. However, in order to preclude tilting or jamming it is an advantage if more than one, especially three, such projections are provided that serve as cams engaging the thread.

Preferably, the touching element is seated, at least in part, in the intermediate piece which may be configured as a sleeve, for example. The smaller the adjusted puncturing depth, the greater will be the length by which the touching element projects from the intermediate piece. Having the touching element enclosed by the intermediate piece makes the lancing device easier to clean. It is preferred in this connection that, when a minimum puncturing depth is adjusted, the touching element should be enclosed by the intermediate piece over the greatest part of its length.

Preferably, the lancing device comprises a rail by means of which it can be attached to a measuring device, as known from EP 1 032 307 B1. A measuring device with an attached lancing device constitutes a system that allows a user to obtain and evaluate a sample of a body fluid. Such a system can be operated using one hand only, for first withdrawing by a puncturing operation, and then evaluating a sample, for example for measuring a glucose concentration.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein:

FIG. 1a shows one embodiment of a lancing device according to the invention;

FIG. 1b shows an embodiment of a measuring device that can be used together with the lancing device of FIG. 1a;

FIG. 1d shows an exploded view relative to FIG. 1a;

FIG. 2 shows the puncturing depth adjusting unit of the lancing device;

FIG. 3 shows a sectional view relative to FIG. 2;

FIG. 4 shows a side view relative to FIG. 2;

FIG. 5 shows a sectional view of the puncturing depth adjusting unit with the touching element in its withdrawn position;

FIG. 6 shows a side view relative to FIG. 5;

FIG. 7 shows an exploded view of the puncturing depth adjusting unit; and

FIG. 8 shows a sectional view relative to FIG. 7.

Skilled artisans will appreciate that elements in the figures are illustrated for simplicity and clarity and have not necessarily been drawn to scale. For example, the dimensions of some of the elements in the figures may be exaggerated relative to other elements to help improve understanding of the embodiments of the present invention.

DETAILED DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

For the purposes of describing and defining the present invention it is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

Figures 1A, 1B:
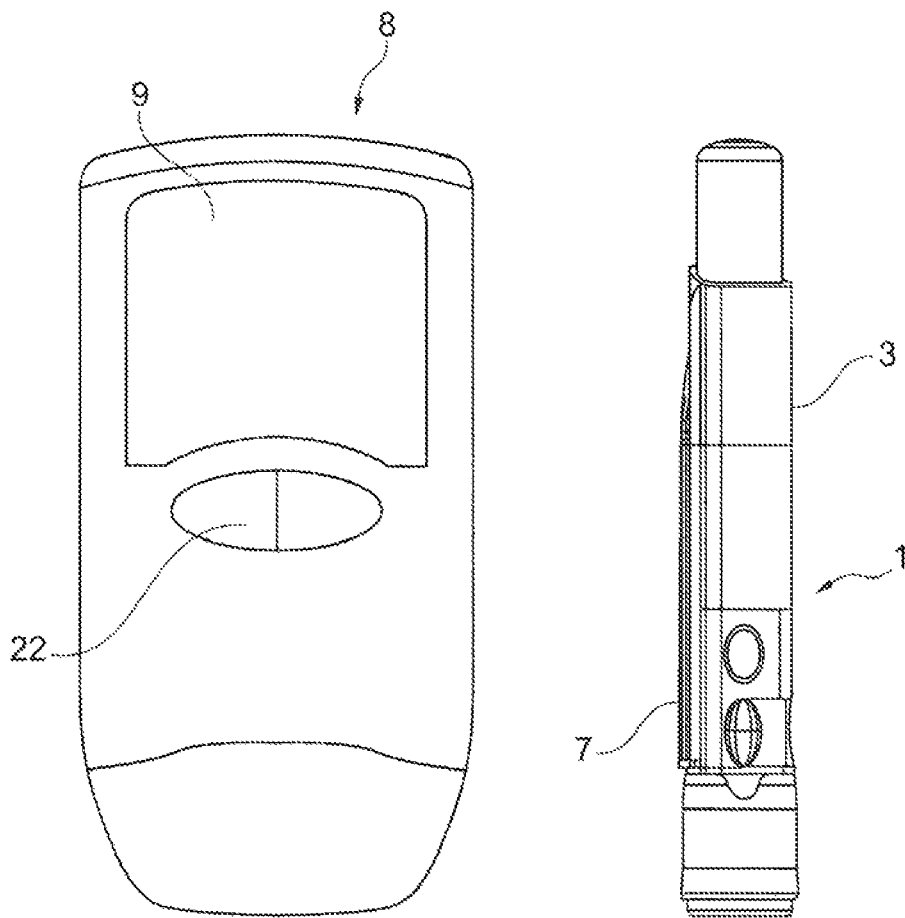
Figure 1C:
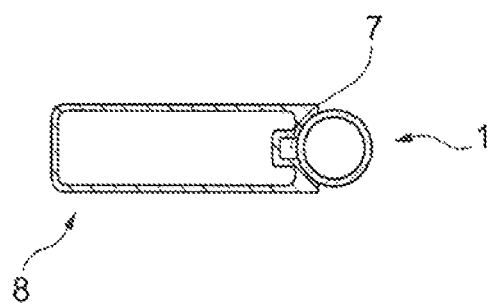
FIG. 1c shows a diagrammatic sectional view of the lancing device illustrated in FIG. 1a, with the measuring device attached.
Figure 1D:
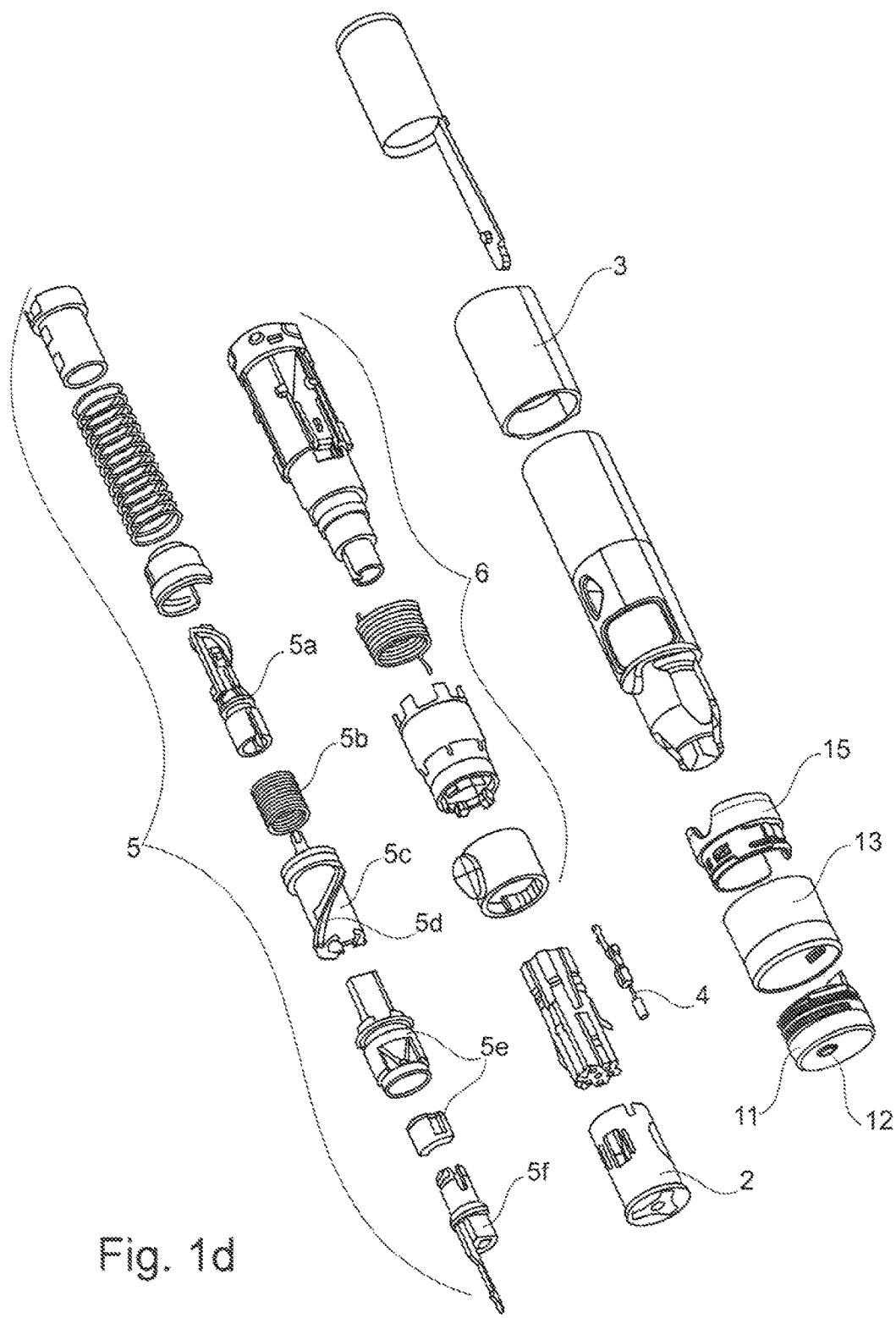

FIGS. 1a and 1d show an embodiment of a lancing device 1 with an associated rotary magazine 2 containing a plurality of lancets 4. The lancing device 1 has a housing 3 that encloses a lancet drive 5. Suitable lancet drives, by which lancets can be caused to perform a puncturing movement, have been widely known in the art and will therefore not be discussed here in more detail. Particularly advantageous solutions are achieved especially with rotor drives where a tensioning element 5a is turned to tension a drive spring 5b which then, when a puncturing action is to be performed, acts to rotate a drive rotor 5c that comprises a control cam 5d which, via a coupling mechanism 5e, causes a lancet holder 5f to perform an advancing movement by which a lancet 4 of the rotary magazine 2 is advanced and is later withdrawn again so that a prick wound is produced in a part of a body applied to the opening 12 of the device.

The lancing device 1 further comprises a stepping mechanism 6 for rotating a loaded rotary magazine by steps so that the lancets 4, which are arranged in the mechanism in ring form, can successively be brought into alignment with the opening 12 for performing a puncturing operation.

The lancing device 1 is provided on one side with a rail 7 by which it can be attached to a measuring device 8 illustrated in FIG. 1b. FIG. 1c shows a diagrammatic sectional view of the measuring device 8 with the lancing device 1 attached. As can be seen in FIG. 1c, for mounting the lancing device 1 on the measuring device 8, it is fitted on the latter in such a way that its rail 7 engages a matching recess of the measuring device 8.

The measuring device 8 is typically provided with a display 9 for displaying measuring results and with operating elements (e.g., buttons) 22 for operation of the device. Generally, the measuring device 8 may be configured in the same way as commercially available devices intended to measure the glucose concentration of a blood sample, and may for example use test elements that permit the concentration to be determined by photometric or electrochemical means. By mounting the lancing device 1 on the measuring device 8, one obtains a system that can be operated by a single hand to perform a puncturing operation for withdrawal of a sample and to take up the sample so obtained for measuring.

The particularity of the illustrated lancing device 1 lies in a puncturing depth adjusting unit 10 illustrated in FIGS. 2 to 8. The puncturing depth adjusting unit 10 comprises a touching element 11 with an opening 12 intended to be applied to a part of a body in which a prick wound is to be produced, and an intermediate piece 13 on which the touching element 11 is fastened by means of a thread 14 illustrated in FIG. 7 so that it can rotate and move in the puncturing direction. It is an advantage that in this way the puncturing depth can be adjusted without any difficulty even with the lancing device 1 mounted on the measuring device 8.

In the illustrated embodiment, the intermediate piece 13 is fastened on a carrier 15 that can be detached from the device housing 3. In principle, however, there is also the possibility to integrate the carrier 15 into the housing 3 and to fasten the intermediate piece 13 directly on the housing 3.

Because of the thread 14 acting between the two parts, rotation of the intermediate piece 13 relative to the touching element 11 causes the touching element 11 to be moved in the puncturing direction. Considering that the lancet drive produces the same lancet travel for every puncturing movement, the puncturing depth will get smaller as the spacing between the touching element 11 and the housing 3 and/or the carrier 15 increases. However, when the spacing between the touching element 11 and the housing 3 and/or the carrier 15 is reduced, i.e. when the touching element 11 is screwed deeper into the intermediate piece 13, this leads to a greater puncturing depth. FIGS. 2 to 4 show the puncturing depth adjusting unit 10 in an end position for a small puncturing depth while FIGS. 5 and 6 show it in an end position for a great puncturing depth.

In the illustrated embodiment, the thread 14 acting between the touching element 11 and the intermediate piece 13 comprises a groove disposed in the touching element 11. That groove is engaged by projections 16 provided on the inside of the intermediate piece 15. It is also possible to dispose corresponding projections 16 on the touching element 11 and to provide the intermediate piece 15 with a complete thread.

The puncturing depth adjusting unit 10 has a linear guide 17a, 17b that prevents any rotary movement of the touching element 11 relative to the carrier 15 and, accordingly, relative to the housing 3. The guide 17a, 17b consists of a guide element 17b that extends in the puncturing direction and that engages between two stops 17b, similar to a groove-and-tongue joint, being movable relative to the two stops in the puncturing direction. In the illustrated embodiment, the guide element 17a is configured as a tongue that engages a matching recess in the carrier 15.

The guide 17a, 17b ensures that the eccentrically arranged opening 12 of the touching element 11 will always retain its orientation relative to the housing 3 and, accordingly, relative to the lancet drive contained in it, irrespective of the adjusted puncturing depth, and that consequently the lancet of a loaded rotary magazine which is to be used next is properly oriented and aligned flush with the opening 12.

The intermediate piece 13, in the form of a sleeve, and the annular carrier 15 are locked in position relative to each other. This locking effect is achieved in the illustrated embodiment by one or more projections 18 of the carrier 15 engaging an annular groove 19 of the intermediate piece 13. In this way, the intermediate piece 13 can rotate relative to the carrier 15 while being simultaneously fixed in the axial direction. There is, however, also the possibility to connect the intermediate piece 13 rotatably with the housing via a further thread. The thread that connects the touching element 11 rotatably with the intermediate piece 13 is oppositely directed in that case to that second thread by which the intermediate piece 13 is rotatably connected with the housing 3, for example via the carrier 15.

The carrier 15 can be detached from the housing 3 of the lancing device 1 for the purpose of replacing a rotary magazine 2 in the receptacle of the lancing device 1 provided for this purpose. In the illustrated embodiment, the rotary magazine 2 is arranged in the puncturing depth adjusting unit formed by the carrier 15, the intermediate piece 13 and the touching element 11.

In the illustrated embodiment, the carrier 15 is locked in position relative to the housing 3 and is provided for this purpose with corresponding locating elements 20 which in the illustrated embodiment take the form of recesses that are engaged by matching locating elements of the housing 3. On its bottom surface facing the housing 3 the carrier 15 exhibits an indentation 21 that is engaged by a fixing element on the housing 3 to retain the carrier 15 against rotation in a predefined position on the housing 3.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMERALS

1 Lancing device
2 Rotary magazine
3 Housing
4 Lancet
5 Lancet drive
5a Tensioning element
5b Drive spring
5c Drive rotor
5d Control cam
5e Coupling mechanism
5f Lancet holder
6 Stepping mechanism
7 Rail
8 Measuring device
9 Display unit
10 Puncturing depth adjusting unit
11 Touching element
12 Opening
13 Intermediate piece
14 Thread
15 Carrier
16 Projection
17a Guide
17b Guide
18 Projections
19 Annular groove
20 Locating element
21 Indentation
22 Operating elements

What is claimed is:
1. A lancing device comprising:
a lancet drive adapted to drive a lancet to effect a puncturing movement;
a housing that encloses the lancet drive; and
a touching element comprising an opening for applying to a part of a body in which a prick wound is to be produced, the touching element being movable to adjust the puncturing depth in the puncturing direction relative to the lancet drive, wherein:

the touching element is adapted to directly contact the body when the prick wound is produced, the touching element is rotatably connected by a screw thread to an intermediate piece and is movable in the puncturing direction, the intermediate piece is rotatable relative to the housing, the lancing device comprises a guide that prevents any rotary movement of the touching element relative to the housing, and the touching element is enclosed by the intermediate piece at least over part of its length.

2. The lancing device of claim 1, wherein the guide comprises a guide element that extends in the puncturing direction and is arranged between two stops relative to which it is movable in the puncturing direction.

3. The lancing device of claim 2, wherein the guide element is configured as a lug disposed on the touching element.

4. The lancing device of claim 1, wherein the screw thread comprises a groove in the touching element.

5. The lancing device of claim 4, wherein at least one projection is disposed on an inner surface of the intermediate piece and engages the groove.

6. The lancing device of claim 1, wherein the intermediate piece comprises a sleeve.

7. The lancing device of claim 1, wherein the housing comprises a detachable carrier on which the intermediate piece is locked in position.

8. The lancing device of claim 7, further comprising a receptacle for holding a rotary magazine wherein the receptacle is adapted to be opened for replacement of the rotary magazine by removing the detachable carrier.

9. The lancing device of claim 8, wherein the receptacle is arranged in a lancing device adjusting unit comprising the detachable carrier, the intermediate piece and the touching element.

10. The lancing device of claim 7, wherein the detachable carrier is secured against rotation and locked in position on the housing.

11. The lancing device of claim 7, wherein the bottom surface of the detachable carrier which faces the housing comprises an indentation that is engaged by a fixing element disposed on the housing.

12. The lancing device of claim 1, wherein the touching element comprises a screw cap.

13. A lancing system comprising the lancing device of claim 1 and a rotary magazine comprising a plurality of lancets.

14. A puncturing depth adjusting unit for a lancing device adapted to produce a prick wound by use with a lancet, the puncturing depth adjusting unit comprising:

a touching element with an opening for applying a part of a body in which a prick wound is to be produced, the touching element adapted to directly contact the body when the prick wound is produced;

an intermediate piece on which the touching element is fastened by a thread to allow it to rotate and to move in a puncturing direction;

a carrier on which the intermediate piece is rotatably and movably fastened; and a guide preventing any rotary movement of the touching element relative to the carrier, wherein the touching element is enclosed by the intermediate piece at least over part of its length.

15. A lancing device comprising:

a lancet drive adapted to drive a lancet to effect a puncturing movement;

a housing that encloses the lancet drive;

a touching element comprising an opening for applying to a part of a body in which a prick wound is to be produced, the touching element being movable to adjust the puncturing depth in a puncturing direction relative to the lancet drive, wherein:

the touching element is adapted to directly contact the body when the prick wound is produced, the touching element is rotatably connected by a screw thread to an intermediate piece and is movable in the puncturing direction, and the intermediate piece is rotatable relative to the housing;

a guide that prevents rotation of the touching element relative to the housing, wherein rotating the touching element and the intermediate piece relative to one another to adjust puncturing depth does not change the rotational orientation of the touching element relative to the housing; and the touching element is enclosed by the intermediate piece at least over part of its length.

16. The lancing device of claim 15, wherein the guide comprises a guide element that extends in the puncturing direction and is arranged between two stops relative to which it is movable in the puncturing direction.

17. The lancing device of claim 15, wherein the guide connects the touching element to a carrier that is fixed relative to the housing.

18. The lancing device of claim 15, wherein the guide extends in the puncturing direction and is arranged between two stops which prevent rotation of the guide.

19. The lancing device of claim 18, wherein the guide comprises a tongue and the two stops form a groove in which the tongue is arranged.

20. A lancing device comprising:

a lancet drive adapted to drive a lancet to effect a puncturing movement;

a housing that encloses the lancet drive;

a touching element comprising an opening for applying to a part of a body in which a prick wound is to be produced, the touching element being movable to adjust the puncturing depth in a puncturing direction relative to the lancet drive, wherein:

the touching element is adapted to directly contact the body when the prick wound is produced, the touching element is rotatably connected by a screw thread to an intermediate piece and is movable in the puncturing direction, and the intermediate piece is rotatable relative to the housing;

a guide that prevents rotation of the touching element relative to the housing, wherein there is no rotary movement between the touching element and the housing when the touching element and intermediate piece are rotated relative to one another to adjust puncturing depth; and the touching element is enclosed by the intermediate piece at least over part of its length.

21. The lancing device of claim 20, wherein the guide comprises a guide element that extends in the puncturing direction and is arranged between two stops relative to which it is movable in the puncturing direction.

22. The lancing device of claim 20, wherein the guide connects the touching element to a carrier that is fixed relative to the housing.

23. The lancing device of claim 20, wherein the guide extends in the puncturing direction and is arranged between two stops which prevent rotation of the guide.

24. The lancing device of claim 23, wherein the guide comprises a tongue and the two stops form a groove in which the tongue is arranged.

25. A lancing device comprising:
- a lancet drive adapted to drive a lancet to effect a puncturing movement;
- a housing that encloses the lancet drive;
- a touching element comprising an opening for applying to a part of a body in which a prick wound is to be produced, the touching element being movable to adjust the puncturing depth in a puncturing direction relative to the lancet drive, wherein:
  - the touching element is adapted to directly contact the body when the prick wound is produced,
  - the touching element is rotatably connected by a screw thread to an intermediate piece and is movable in the puncturing direction, and
  - the intermediate piece is rotatable relative to the housing;
- a guide that prevents rotation of the touching element relative to the housing when the touching element and intermediate piece are rotated relative to one another to adjust puncturing depth; and
- the touching element is enclosed by the intermediate piece at least over part of its length.

26. The lancing device of claim 25, wherein the guide comprises a guide element that extends in the puncturing direction and is arranged between two stops relative to which it is movable in the puncturing direction.

27. The lancing device of claim 25, wherein the guide connects the touching element to a carrier that is fixed relative to the housing.

28. The lancing device of claim 25, wherein the guide extends in the puncturing direction and is arranged between two stops which prevent rotation of the guide.

29. The lancing device of claim 28, wherein the guide comprises a tongue and the two stops form a groove in which the tongue is arranged.

* * * * *